United States Patent [19]

Watt et al.

[11] Patent Number: 4,566,114
[45] Date of Patent: Jan. 21, 1986

[54] X- AND γ-RAY TECHNIQUES FOR DETERMINATION OF THE ASH CONTENT OF COAL

[75] Inventors: John S. Watt, Heathcote; Reginald A. Fookes, Caringbah; Vilis L. Gravitis, Revesby, all of Australia

[73] Assignee: Australian Atomic Energy Commission, Coogee, Australia

[21] Appl. No.: 411,403

[22] Filed: Aug. 25, 1982

Related U.S. Application Data

[63] Continuation-in-part of Ser. No. 161,252, Jun. 20, 1980, abandoned.

[51] Int. Cl.⁴ .................................... G01N 23/20
[52] U.S. Cl. ................................ 378/88; 250/255; 250/359.1
[58] Field of Search ............ 250/358.1, 359.1, 252.1, 250/255; 378/88, 86, 53

[56] References Cited

U.S. PATENT DOCUMENTS

| | | | |
|---|---|---|---|
| 2,997,586 | 8/1961 | Scherbatskoy . | |
| 3,983,392 | 9/1976 | Armstrong | 378/88 |
| 4,034,218 | 7/1977 | Turcotte | 250/269 |
| 4,090,074 | 5/1978 | Watt et al. | 378/53 |

FOREIGN PATENT DOCUMENTS

| | | |
|---|---|---|
| 18592 | 6/1979 | Australia . |
| 872966 | 6/1971 | Canada . |
| 931668 | 8/1973 | Canada . |
| 750328 | 6/1956 | United Kingdom . |
| 973709 | 10/1964 | United Kingdom . |
| 1033789 | 6/1966 | United Kingdom . |
| 1065919 | 4/1967 | United Kingdom . |
| 1067430 | 5/1967 | United Kingdom . |
| 1531572 | 11/1978 | United Kingdom . |

Primary Examiner—Alfred E. Smith
Assistant Examiner—Carolyn E. Fields
Attorney, Agent, or Firm—Ladas & Parry

[57] ABSTRACT

X- or γ-ray scatter assemblies are used in quantitative determination of the concentration of ash in coke or coal. The assemblies each comprise an X- or γ-ray source, an energy sensitive detector to detect X- or γ-rays resulting from scatter in the coal or coke of X- or γ-rays from the source, and shielding means adapted to reduce the intensity of direct X-rays or γ-rays and to collimate partly the beam of X-rays and or γ-rays to ensure maximized matched volumes for all assemblies and deep penetration in the coal. The assemblies are associated with an electronic analyzer adapted to select all or part of the detected X-ray or γ-ray spectrum, thereby modifying the output of the assemblies. Two or more assemblies are employed in an apparatus and method for analyzing coal or coke.

11 Claims, 5 Drawing Figures

X- AND γ-RAY TECHNIQUES FOR DETERMINATION OF THE ASH CONTENT OF COAL

The instant application is a continuation-in-part of earlier-filed application Ser. No. 161,252, filed June 20, 1980, now abandoned.

The present invention relates to improvements in the determination of the ash content of coal or coke employing measurements of X-rays and/or γ-rays. The application of X-ray and/or γ-ray techniques to determine ash content of coal or coke is described by J. S. Watt and V. L. Gravitis in "Analysis of Coal" U.S. Pat. No. 4,090,074, the disclosure of which is incorporated herein by reference.

Accurate analysis of coal is made difficult by its heterogeneous nature. For example, coal on conveyor belts is known to segregate on different parts of the belt depending on its particle size and density. As a result the composition of small samples may differ in ash content, particle size distribution and density from that of the average of large samples. It is therefore desirable to average the ash content determination over as large a volume of coal as possible so that an analysis representative of the whole coal sample or coal stream to be analyzed is obtained.

In practice, using X-ray or γ-ray techniques, this would be achieved by detecting the X-rays or γ-rays which have penetrated deeply into the coal.

If ash content is determined by combining measurements from two or more X-ray and/or γ-ray assemblies, accurate ash determination would require that essentially the same volume of coal is "seen" by each separate measurement, i.e., the detected X-ray intensity, for each measurement has resulted from interactions of X-rays or γ-rays over the same volume of coal. Since the mass absorption coefficient of X-rays or γ-rays in coal changes considerably with energy, sample volumes "seen" by each X-ray measurement normally overlap only to a limited extent.

U.S. Pat. Nos. 2,997,586 and 4,034,218 describe measurements of the properties of materials using backscatter geometries and tightly collimated beams. Such collimation has the disadvantage that only relatively small volumes of material are "seen". The concept of maximizing matched volumes seen by each of a number of source/detector assemblies to improve analysis results is not mentioned in these patents or in U.S. Pat. No. 4,090,074.

The present invention relates to the determination of ash content of coal using X-ray and/or γ-ray techniques in which the volume of coal "seen" by each separate measurement is approximately the same i.e. "matched", and in which X-rays and/or γ-rays penetrate deeply within the coal. The basis of matching the volumes over as large a volume as possible and obtaining deep penetration, is the use of partial collimation of X-ray and/or γ-ray beams. The separate measurements with matching volumes can be made with two or more assemblies.

The present invention therefore provides a measuring apparatus for quantitative determination of the concentration of ash in coal or coke, which apparatus comprises at least two X-ray or γ-ray scatter assemblies, and means to compute said ash concentration from the outputs of said assemblies, the geometries of said assemblies each being arranged so that the detected X-ray or γ-ray intensity is a measure over substantially the same volume of coal or coke sample, said assemblies each comprising an X-ray or γ-ray source, an energy-sensitive detector to detect said scattered X-rays or γ-rays resulting from scattering in the coal or coke of X-rays or γ-rays from said source, an electronic analyzer associated therewith to select all or one or more parts of the detected X-ray or γ-ray spectrum as output from said assemblies, and shielding means for reducing the intensity of direct X-rays or γ-rays, said shielding means being specifically chosen to collimate partly the beam of X-ray or γ-rays in such way as to ensure maximized matched volumes and deep penetration in the coal, and wherein the energy of the X-rays or γ-rays emitted by said assemblies differ from each other.

In the context of the present invention, a scatter-assembly is one which uses shielding means to greatly reduce any direct radiation from the source reaching the detector. With such shielding, only radiation that has been scattered at least once in a coal sample can reach the detector. A backscatter assembly is one where the source and detector are on the same side of the sample and a scatter-transmission assembly is one where the source and detector are on opposite sides of the sample. In the present invention the term "scatter-assembly" includes both backscatter assembly and scatter-transmission assembly.

In the context of the present invention "same volume" refers to measurements over the same part of a sample. When two or more scatter assemblies are used with static samples in containers, measurement on the same part of the sample is readily achieved by measuring each sample in sequence on various assemblies. For continuous measurements, as with coal on a conveyor belt, the scatter assemblies are mounted in line along the direction of movement of the belt, and the processing of signals is delayed in time until a given sample of coal on the conveyor has passed all the scatter assemblies in sequence, at which stage the ash value for that volume of coal is computed.

Also within the scope of the invention is a method of analyzing coal or coke comprising determining the concentration of ash or mineral matter in coal or coke by the steps comprising measuring the scatter of X-rays or γ-rays of a first energy chosen such there is a significant difference in absorption of radiation per unit weight in coal matter and mineral matter excluding iron, in combination with either or both of (a) effecting at least one further measurement of scatter of X-rays or γ-rays at a different energy so chosen that there is a significant difference in absorption of radiation per unit weight of coal matter and mineral matter and that the relative absorption per unit weights by said coal matter and said mineral matter at any one energy is significantly different from the relative absorption at each other energy including said first energy, (b) effecting a measurement of the bulk density or mass per unit area of the coal or coke by measuring backscatter or scatter-transmission respectively of X-rays or γ-rays at an energy chosen such that there is no significant difference in absorption of radiation per unit weight in coal matter and mineral matter, and wherein the detected X-ray or γ-ray intensity is measured using scatter assemblies which have maximised matched volumes.

Figure 1:
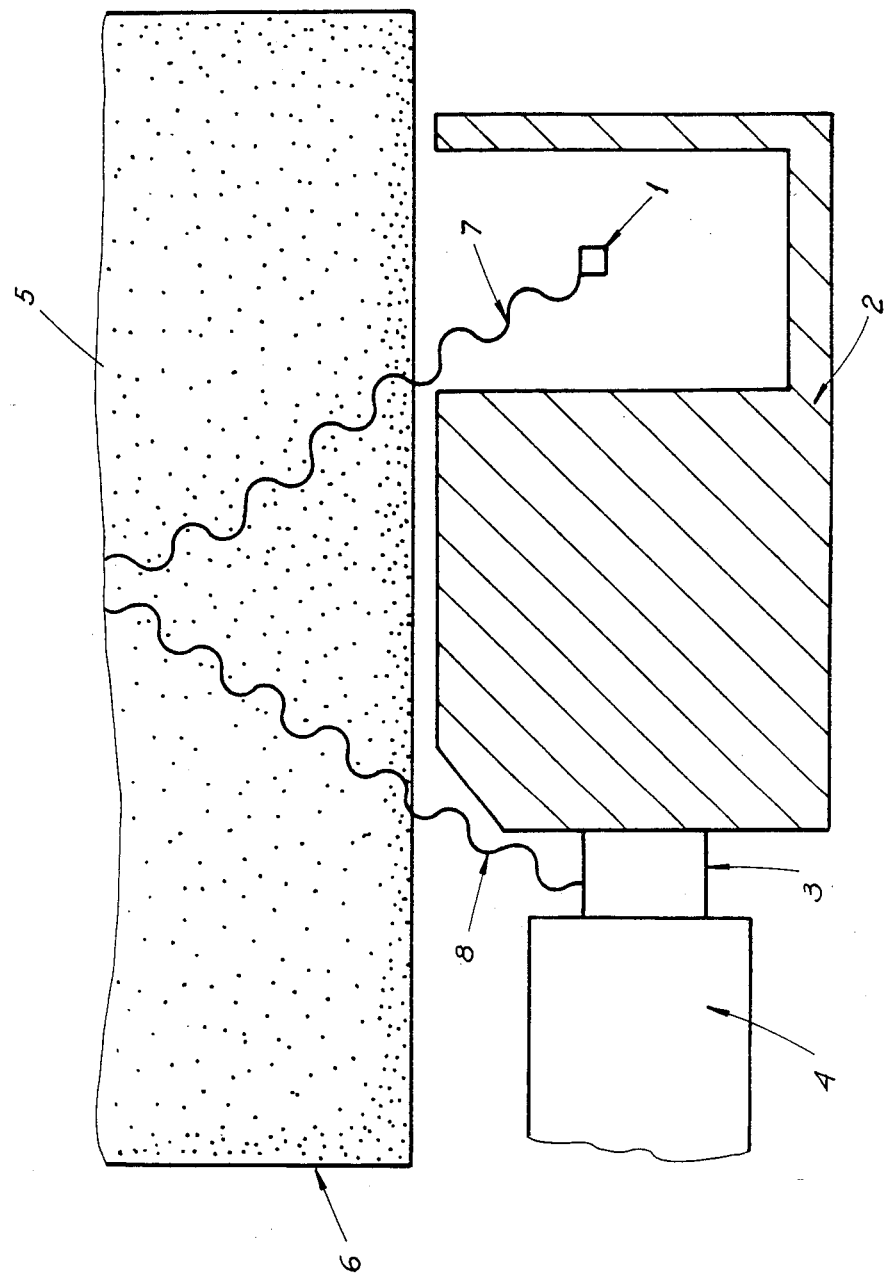
FIG. 1 is an illustration of backscatter assembly suitable for use in the invention.

FIG. 1 shows a geometrical arrangement of an X-ray or γ-ray backscatter assembly showing radioisotope source 1, shielded container 2, scintillation detector 4, with sodium iodide crystal 3, and coal or coke sample 5.

Figure 2:
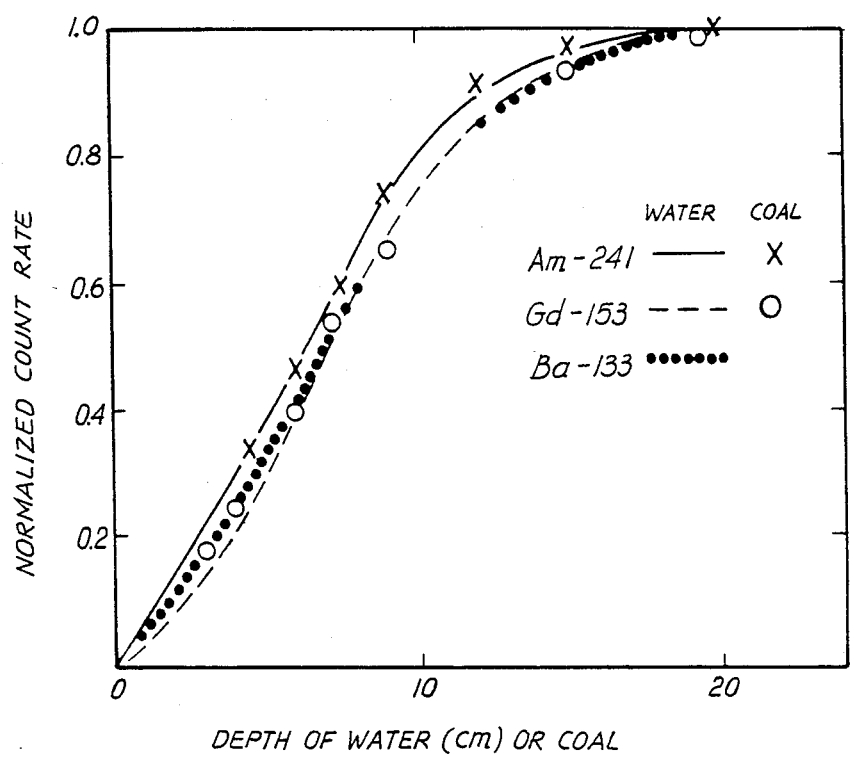
FIG. 2 shows a normalized count rate plotted against depth of water and depth of coal.

FIG. 2 shows a normalized count rate plotted against depth of water and depth of coal determined using Am-241, Gd-153 and Ba-133 radioisotope sources. The effect of depth of sample material on normalized count rate is approximately the same for each source.

The matching of volumes has been obtained by apparatus shown diagrammatically in FIG. 1. The radioisotope source 1, was located within a shielded container 2, and the sodium iodide crystal 3, of a scintillation detector 4, was located against the outside of the shielded container. The coal sample 5, in an aluminum container 6, is placed above the shielded assembly. The path of a γ-ray or X-ray 7, from the radioisotope source scattering in the coal sample, and scattered γ-ray 8, to detector, is also shown. Multiple scatter of γ-rays in the coal sample also occurs, and results in detection of the multi scattered γ-ray.

The measurements described below were all made using the assembly shown in FIG. 1. A sodium iodide crystal of diameter 38 mm, height 25 mm was used, and all X-rays or γ-rays detected were counted by the scintillation detector.

The procedure to maximize the matched volume seen by the three assemblies by using partial collimation is as follows. Firstly, a source to detector distance is chosen which is as large as possible while keeping the intensity of backscattered radiation detected sufficiently high for accurate measurements. With the source to detector distance fixed, a series of measurements of backscattered intensity as a function of sample thickness was made for each of the three radioisotopes used. Both the detector and source holder were then placed lower with respect to the top surface of the shield (see FIG. 1) and the series of measurements was repeated. Lowering the source and detector causes the average depth of penetration of the lowest energy γ-rays (Am-241 60 keV) to increase relative to that of the highest energy γ-rays (Ba-133 356 keV). As the detector and sources were progressively lowered, the effective collimation was increased, and the depth matching of the Am-241, Gd-153 and Ba-133 curves became better until the results in FIG. 2 were obtained. The continuous curves were obtained using water as the sample, and "X" and "O" represent measurements on coal containing 10 wt. % ash. The detected intensity was determined as a function of depth of water or coal in the container for each of the three sources, Am-241 (60 keV γ-rays), Gd-153 (100 keV) and Ba-133 (mainly 356 keV). The normalized count rate (vertical/axis, FIG. 2) was obtained by taking the ratio of measured count rate at the water depth to the count rate obtained for great depths corresponding to saturation of intensity of back-scattered X-rays. FIG. 2 shows that good matching with depth of water or coal sample has been obtained for the three sources used. For Am-241, the effective penetration has been increased by a factor of three compared with that for an uncollimated beam.

The results above demonstrate that good matching has been obtained with each source in exactly the same position in the shielded container. An even closer coincidence of curves in FIG. 2 for Am-241, Gd-153, and Ba-133 could be obtained by altering the Am-241 source position relative to the position of the other two sources or the distance of the assembly from the coal sample. Matching in lateral directions has not been considered above, but can also be achieved by the use of selective collimation of the radioisotope sources.

The use of "matched" volumes is also of advantage when samples of coal are of thickness less than that corresponding to saturation of backscattered intensity of X-rays or γ-rays. The use of "matched" volumes makes it possible for a correction to be applied to compensate for changes in coal depth and hence determine ash content more accurately.

For a scatter/transmission assembly (FIG. 4), matching the volumes of coal or coke "seen" is done by making the collimation identical for all the assemblies used. The assembly with the lowest energy γ-ray source (Am-241 when assemblies with Am-241, Gd-153 and Ba-133 are being used) and with the thickest expected sample in position, is used to fix the maximum volume that can be matched for all the assemblies. With this assembly, the source collimation is decreased (by widening the mouth of the source shield 33 in FIG. 4) until there is no further significant increase in detected intensity by the scintillation detector 35 in FIG. 4. This fixes the amount of source collimation used for all the assemblies.

The following Examples illustrate preferred embodiments of the invention. In each case the coal being analyzed can be a static sample, or in a continuously flowing sample by-line, or the main stream of coal moving on a conveyor or through a hopper.

EXAMPLE 1

Figure 3:
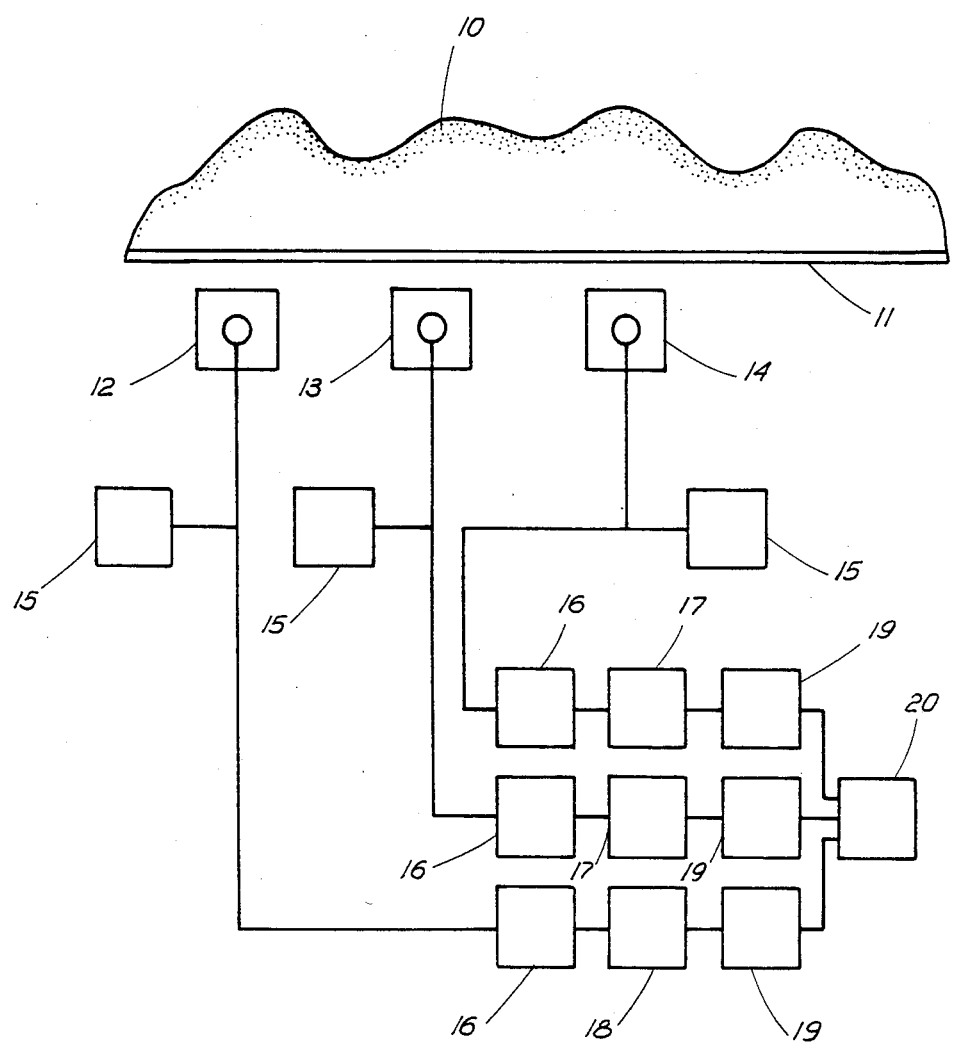
FIG. 3 is a diagrammatic illustration of a preferred embodiment of the invention.

A preferred embodiment of the invention is described in the following example with reference to FIG. 3. Coal 10 on a moving conveyor belt 11 is viewed by beams of X-rays or γ-rays from backscatter assemblies 12, 13 and 14, each substantially similar to that in FIG. 1. The radioisotope sources in each assembly could be Am-241 (59.5 keV), Gd-153 (∼100 keV) and Ba-133 (356 keV and others). However, there are many other combinations of sources that would be suitable, e.g., Sm-145 or a secondary excitation source, Am-241, and Ba-133 or Cs-137. The electronics used with scintillation detectors (4 in FIG. 1) are known art and comprise high voltage units 15 to polarize the scintillation detectors, amplifiers 16, single channel analyzers 17 or discriminator 18 to select electrical pulse heights corresponding to the approprate γ- or X-rays detected, and interface units 19 to link outputs from the units 17, 18 with the digital computer 20 which scales the electrical pulses and calculates the ash content.

The preferred embodiment has been used to determine the ash content of coal samples supplied by Utah Development Co. (ash range 5-27 wt. %, iron in ash 3-19 wt. %, 24 samples). The three radioisotope sources used in the three matched backscatter assemblies were Am-241, Gd-153 and Ba-133. The measured intensities $I_{Am}$, $I_{Gd}$, and $I_{Ba}$ were combined to give the ash content $C_{ash}$ by the equation $$C_{ash} = a_1 + \frac{a_2}{I_{Am}} + \frac{a_3}{(I_{Gd} + a_4)} + \frac{a_5}{I_{Ba}}$$

The rms error in ash content determination for these samples was 1.6 wt. % ash. The subscripted values of "a" in this and the next equation are constants derived by a least squares calculation to give the minimum error in $C_{ash}$.

This error of 1.6 wt. % ash compares with an error of 3.0 wt. % ash for the same samples when using only the measured intensities $I_{Am}$ and $I_{Ba}$ from the matched backscatter assemblies using Am-241 and Ba-133 radioisotope sources.

When selected parts of the measured spectra from the Am-241 and Gd-153 assemblies are used instead of the whole spectra as above, it would be expected that the rms error of 1.6 wt. % ash in ash determination would be decreased.

A simpler form of the preferred embodiment has been used to determine the ash content of coal samples having a more limited range of variation of ash content and iron in the ash. (Samples supplied by Utah Development Co., ash range 5–18 wt. %, iron in ash 6–14 wt. %, 13 samples). As the range of iron concentrations in these samples was not very great, the measurement for ash only had to be corrected for density variations. Only two matched backscatter assemblies were therefore required. The two radioisotopes used in the two matched backscatter assemblies were Am-241 and Ba-133. The measured intensity $I_{Ba}$ is proportional to the bulk density of the coal, and when combined with $I_{Am}$ gives the ash content $C_{ash}$ by the equation $$C_{ash} = a_1 + a_2 \log (I_{Am}) + a_3 \log (I_{Ba}).$$

The rms error in ash content determination for these samples was 1.0 wt. % ash.

EXAMPLE 2

Figure 4:
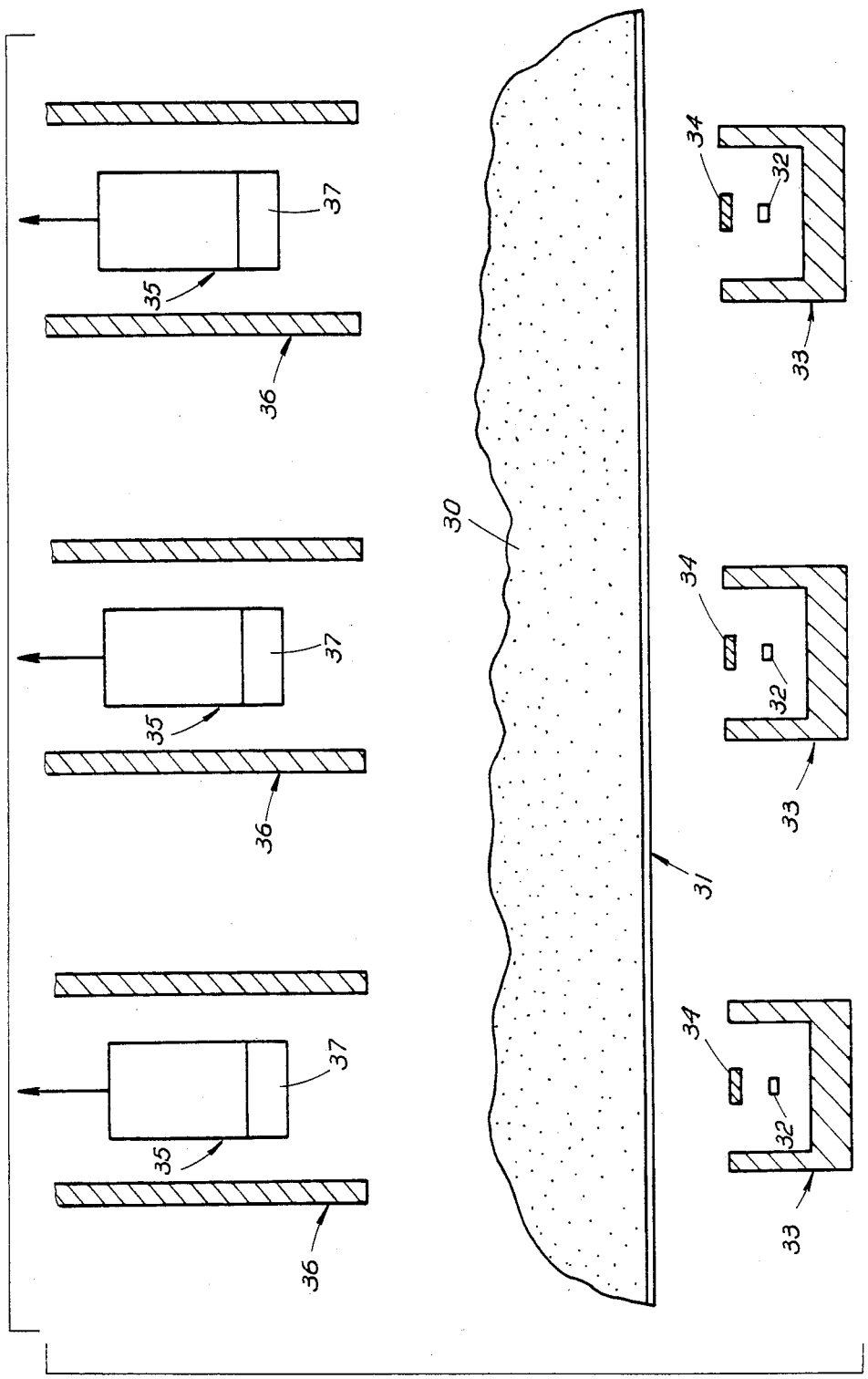
FIG. 4 is an illustration of scatter-transmission assemblies suitable for use in the invention.

A second preferred embodiment is based on scatter-transmission of $\gamma$-rays or X-rays (FIG. 4). The geometrical arrangement of scatter-transmission assemblies about the coal 30 on conveyor 31 comprise radioisotope sources 32, in shielded containers 33, with further shields 34 between sources 32 and scintillation detectors 35, with further shields 36 about the sodium iodide crystals 37 of the scintillation detectors 35. The shields 34 stop $\gamma$-rays or x-rays from the radioisotope sources from reaching the detectors directly, i.e. all detected $\gamma$-rays or X-rays must have resulted from a scattering interaction in the coal. The shields 33 and 36, by limiting the directions of $\gamma$-rays or X-rays incident on the coal and emergent detected $\gamma$-rays or X-rays ensure that most of the detected $\gamma$-rays or X-rays have resulted from interactions in the same "sensitive" volume of coal. Hence the sensitive volume is matched for various energy $\gamma$-rays.

The electronic equipment is similar to that described in Example 1.

If one of the above assemblies is used with a Ba-133 source, the measured intensity from that assembly will be proportional to the mass per unit area of the coal on the conveyor.

The sources of X- and $\gamma$-rays described hereinabove are illustrative only of suitable sources. Other known sources are Co-57 and Cd-109 and those described in U.S. Pat. No. 4,090,074, the disclosure of which is incorporated herein by reference, will be apparent to those skilled in the art.

EXAMPLE 3

Figure 5:
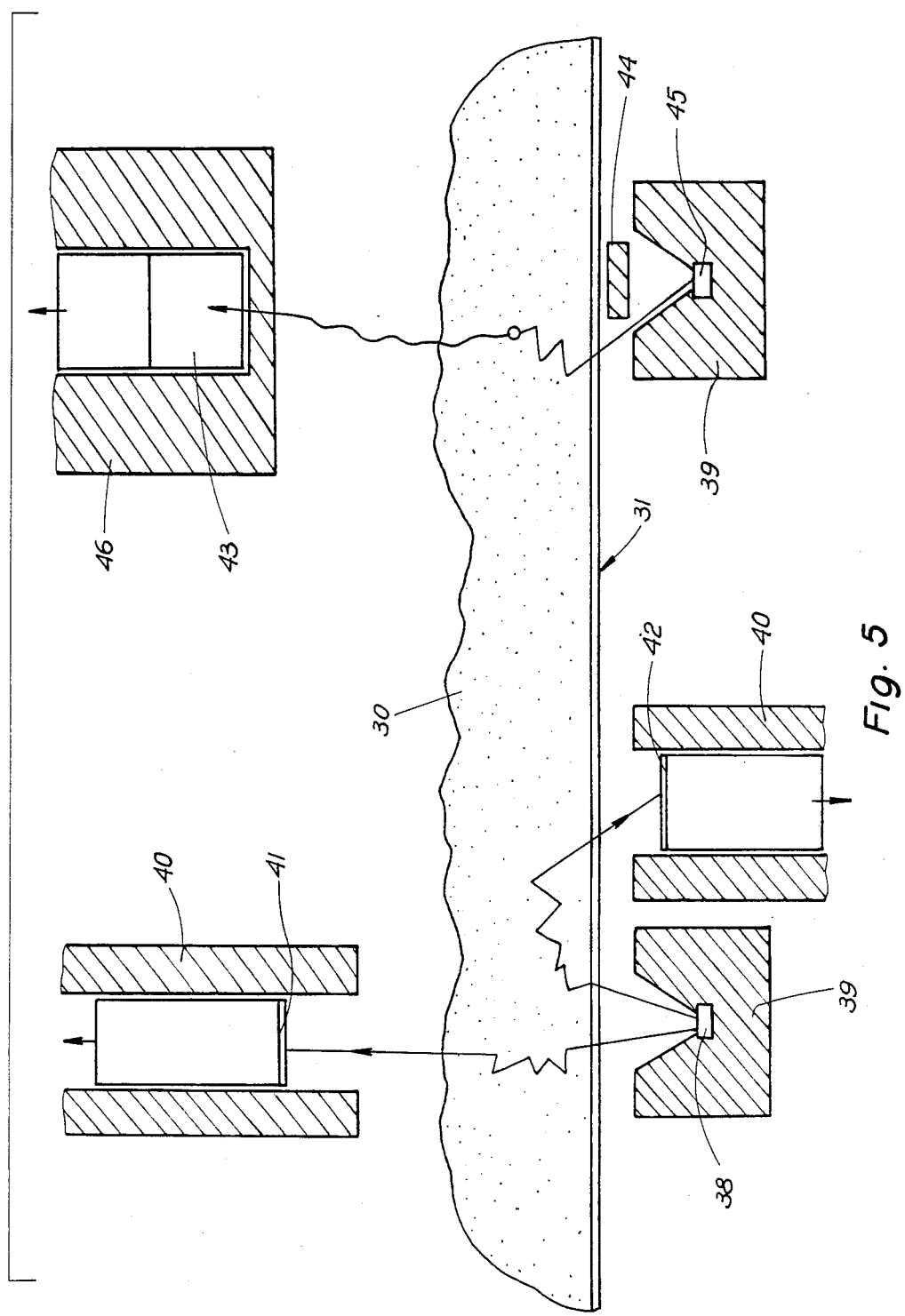
FIG. 5 is an illustration of assemblies suitable for use in measuring hydrogen or moisture or iron content by neutron techniques.

A third preferred embodiment uses one or more neutron assemblies in addition to one of the two scatter assemblies already described. This may be sometimes necessary when a correction for variations in hydrogen or moisture or iron is needed to give the most accurate measurement of ash content of coal or coke. Hydrogen or moisture can be determined by either neutron transmission or backscatter or by a capture $\gamma$-ray technique. In FIG. 5 a neutron source 38 (californium-252, plutonium-238/beryllium or americium-241/beryllium) is contained in a neutron shielding material 39 open at the end facing the conveyor 31. Transmitted thermal neutrons can be measured by a thermal neutron detector 41 and scattered neutrons can be measured by a thermal neutron detector 42. All detectors are shielded with thermal neutron shields 40 as shown. Both measurements of thermal neutron intensity are proportional to hydrogen or moisture content of the coal 30. Hydrogen or moisture or iron in the coal can also be determined by measuring the capture $\gamma$-rays of hydrogen (2.23 MeV energy) or the capture $\gamma$-rays of iron (approximately 7.6 MeV energy) by using an energy sensitive $\gamma$-ray detector 43 in thermal neutron shield 46. In this case a lead shield 44 is used to shield direct $\gamma$-rays from the neutron source 45 (any of the abovementioned sources) from reaching the detector 43. The electronic equipment is similar to that described in Example 1.

In practice only one of the methods for measuring hydrogen or moisture would be used in any one case.

We claim:

1. A measuring apparatus for quantitative determination of the concentration of ash in coal or coke, which apparatus comprises at least two X-ray or $\gamma$-ray scatter assemblies, and means to compute said ash concentration from the outputs of said assemblies, the geometries of said assemblies each being arranged so that the detected X-ray or $\gamma$-ray intensity is a measure over substantially the same amount by volume of coal or coke sample, said assemblies each comprising an X-ray or $\gamma$-ray source, an energy-sensitive detector to detect scattered X-rays or $\gamma$-rays resulting from scattering in the coal or coke of X-ray or $\gamma$-rays from said source, an electronic analyzer associated therewith to select all or one or more parts of the detected X-ray or $\gamma$-ray spectrum as output from said assemblies, and shielding means for reducing the intensity of direct X-rays or $\gamma$-rays, said shielding means being specifically chosen to collimate partly the beam of X-rays or $\gamma$-rays in such way as to ensure maximized matched volumes and deep penetration in the coal or coke, and wherein the energy of the X-rays or $\gamma$-rays emitted by said assemblies differs from each other.

2. An assembly as defined in claim 1, wherein the source of X- or $\gamma$-rays is selected from the group consisting of Am-241, Gd-153, Ba-133, Cd-109, Cs-137 and Co-57.

3. A measuring apparatus as defined in claim 1, wherein said scatter assembly has its source and detector on the same side of said coal or coke sample.

4. A measuring apparatus as defined in claim 1, wherein said scatter assembly has its source and detector on opposite sides of said coal or coke sample.

5. A measuring apparatus as defined in claim 1, further comprising one or more measuring means which measure moisture content, hydrogen content, or iron content.

6. A method of analyzing coal or coke comprising determining the concentration of ash or mineral matter in coal or coke by the steps comprising measuring the scatter of X-rays or γ-rays of a first energy chosen such that there is a significant difference in absorption of radiation per unit weight in coal matter and mineral matter excluding iron, in combination with either or both of (a) effecting at least one further measurement of scatter of X-rays or γ-rays at a different energy so chosen that there is a significant difference in absorption of radiation per unit weight of coal matter and mineral matter and that the relative absorption per unit weights by said coal matter and said mineral matter at any one energy is significantly different from the relative absorption at each other energy including said first energy, (b) effecting a measurement of the bulk density or mass per unit area of the coal or coke by measuring the backscatter or scatter-transmission respectively of X-rays or γ-rays at an energy chosen such that there is no significant difference in absorption of radiation per unit weight in coal matter and mineral matter, and wherein the detected X-ray or γ-ray intensity is, measured using scatter assemblies which detect radiation from maximised matched volumes.

7. A method as defined in claim 6, wherein the step (a) is constituted by scatter of X-rays or γ-rays at one further energy chosen that there is a significant difference in absorption of radiation per unit weight in coal matter and mineral matter and that the relative absorption per unit weights by said coal matter and said mineral matter at said first energy is significantly different from the relative absorption at said further energy.

8. The method wherein the concentration of ash or mineral matter in coal or coke is determined as defined in claim 7, coupled with a further measurement of iron concentration by neutron capture γ-ray techniques.

9. The method wherein the concentration of ash or mineral matter in coal or coke is determined as defined in claim 6, coupled with a measurement of moisture or hydrogen content.

10. The method as defined in claim 9, wherein the moisture or hydrogen content is measured by neutron scatter or transmission, or capture γ-rays from neutron absorption by hydrogen.

11. The method as defined in claim 6, wherein the X or γ-rays are obtained from radioisotope sources selected from the group consisting of Am-241, Gd-153, Cd-109, Ba-133, Cs-137 and Co-57.

* * * * *